US00H002119H

(19) United States

(12) Statutory Invention Registration (10) Reg. No.: US H2119 H

Clark et al. (43) Published: Jun. 7, 2005

(54) ACOUSTIC FUSION OF AQUATIC ANIMAL TISSUE CELLS WITH BIOLOGICAL AGENTS

(75) Inventors: Joseph A. Clark, Arlington, VA (US); Jane A. Young, Rockville, MD (US)

(73) Assignee: The United States of America as represented by the Secretary of the Navy, Washington, DC (US)

(21) Appl. No.: 08/971,839

(22) Filed: Nov. 17, 1997

(51) Int. Cl.[7] ..... C12N 13/00

(52) U.S. Cl. ..... 435/173.5; 219/215

(58) Field of Search ..... 435/173.5; 119/2, 119/3, 4; 601/2

(56) References Cited

U.S. PATENT DOCUMENTS

| | | | | |
|---|---|---|---|---|
| 4,578,168 A | | 3/1986 | Hofmann | 435/285.2 |
| 4,695,547 A | | 9/1987 | Hilliard et al. | 435/285.2 |
| 4,764,473 A | | 8/1988 | Matschke et al. | 435/285.2 |
| 4,780,212 A | * | 10/1988 | Kost et al. | 210/646 |
| 4,923,814 A | | 5/1990 | Marshall | 435/173.6 |
| 4,945,050 A | | 7/1990 | Sanford et al. | 435/459 |
| 4,948,587 A | | 8/1990 | Kost et al. | 424/435 |
| 4,955,378 A | | 9/1990 | Grasso | 607/53 |
| 5,076,208 A | | 12/1991 | Zohar et al. | 119/200 |
| 5,098,843 A | | 3/1992 | Calvin | 435/285.2 |
| 5,128,257 A | | 7/1992 | Baer | 435/173.6 |
| 5,186,800 A | | 2/1993 | Dower | 435/173.6 |
| 5,304,486 A | | 4/1994 | Chang | 435/285.2 |
| 5,422,272 A | | 6/1995 | Papp et al. | 435/285.2 |
| 5,457,041 A | | 10/1995 | Ginaven et al. | 435/455 |
| 5,458,140 A | | 10/1995 | Eppstein et al. | 600/573 |
| 5,516,670 A | | 5/1996 | Kuehnle et al. | 435/459 |
| 5,547,467 A | | 8/1996 | Pliquett et al. | 604/20 |

OTHER PUBLICATIONS

Skauen et al., Int. J. Pharmaceutics, 20(3), "Phonopheresis", pagews 235–245, 1984.*

Baltimore Sun, Apr. 13, "Company Aims to Help Fish Grow Faster", p. C11, 1993.*

Fish Farm News, vol. 4, vp., "Ultrasound Enhances Delivery of Drugs, Vaccines, to Fish: Commercial Use Anticipated", 1996.*

Alliger, Heat Systems—Ultrasonics, Inc., Plainview, New York, "Instruction Manual, Sonicator Cell Disruptor Models W–220F and W–225R", pp. i–8, 1980.*

Monaghan, J.P. Jr., Transactions of the American Fisheries Society, vol. 122, No. 2, "Comparison of Calcein and Tetracycline as Chemical Markers in Summer Flounder", pp. 298–301, 1993.*

Cohen, A., Nor'Easter, vol. 7, No. 1, "Sound Ways of Keeping Farmed Fish Healthy", pp. 28–31, Spr 1995.*

Cohen, A., Fish Farm News, vol. 4, "Ultrasound Enhances Delivery of Drugs, Vaccines to Fish: Commercial Uses Anticipated", pp. 5 and 26 (full text of article previously cited), Jan. 1996.*

Mohler, J.W., North American Journal of Fisheries Management, vol. 17(3), "Immersion of Larval Atlantic Salmon in Calcein Solutions to Induce a Non–lethally Detectable Mark", pp. 751–756, in BIOSIS: AN 1998:31044, Aug. 1997.*

Monaghan, J. P. Jr., Transactions of the American Fisheries Society, vol. 122(2), "Comparison of Calcein and Tetracycline as Chemical Markers in Summer Flounder", pp. 298–301, in BIOSIS: AN 1993:408428, 1993.*

Heat Systems Ultrasonics, "Sonicator Series Application Notes—Breaking the Heat Barrier", AN–1, pp. 1–2, Nov. 1977.*

* cited by examiner

*Primary Examiner*—Harvey E. Behrend

(74) *Attorney, Agent, or Firm*—Jacob Shuster

(57) ABSTRACT

Biological agents in solution within an underwater treatment zone are transferred by infusion to living cells under an acoustic energy field of limited duration and certain accompanying water flow and temperature conditions to maximize processing efficiency.

12 Claims, 2 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

ACOUSTIC FUSION OF AQUATIC ANIMAL TISSUE CELLS WITH BIOLOGICAL AGENTS

The present invention relates in general to the perforation of living cells during delivery thereto of biological agents for various purposes including tagging and DNA infusion.

BACKGROUND OF THE INVENTION

A process for transfer of chemical agents within some surrounding medium through living tissue referred to as poration, is well known in the art as disclosed for example in U.S. Pat. No. 5,128,257 to Baer. Generally, such process involves generation of electrical energy forming an electrical field between electrodes within which electroporation occurs. The generation of an ultra-sound acoustic field within which different chemical compounds are administered by delivery to the tissue cells of aquatic animals or their eggs for fish farm treatment purposes, is disclosed in U.S. Pat. No. 5,076,208 to Zohar et al. However, infusion of animal tissue cells with biological agents such as tagging compounds was heretofore performed by electroporation subject to various disadvantages such as tissue cell disruption by high voltage and reduced processing efficiency because of limits imposed on the number of tissue cells capable of being simultaneously processed. It is therefore an important object of the present invention to provide an improved process for infusion of biological material into living tissue cells of relatively large aquatic animal populations within underwater environments with improved efficiency.

SUMMARY OF THE INVENTION

In accordance with the present invention, large numbers of aquatic animals are serviced by poration and fusion of their tissue cells with certain biological compounds transferred from solution within an underwater treatment zone. The poration and infusion process is performed within the treatment zone under an acoustic energy field of limited duration produced by amplification of a steady state electrical power signal converted into ultrasound waves within a cavitation frequency range establishing the acoustic field within the treatment zone. The tissue cells after being so treated are extracted from the treatment zone.

BRIEF DESCRIPTION OF DRAWING FIGURES

A more complete appreciation of the invention and many of its attendant advantages will be readily appreciated as the same becomes better understood by reference to the following detailed description when considered in connection with the accompanying drawing wherein.

DETAILED DESCRIPTION OF PREFERRED EMBODIMENTS

Figure 1:
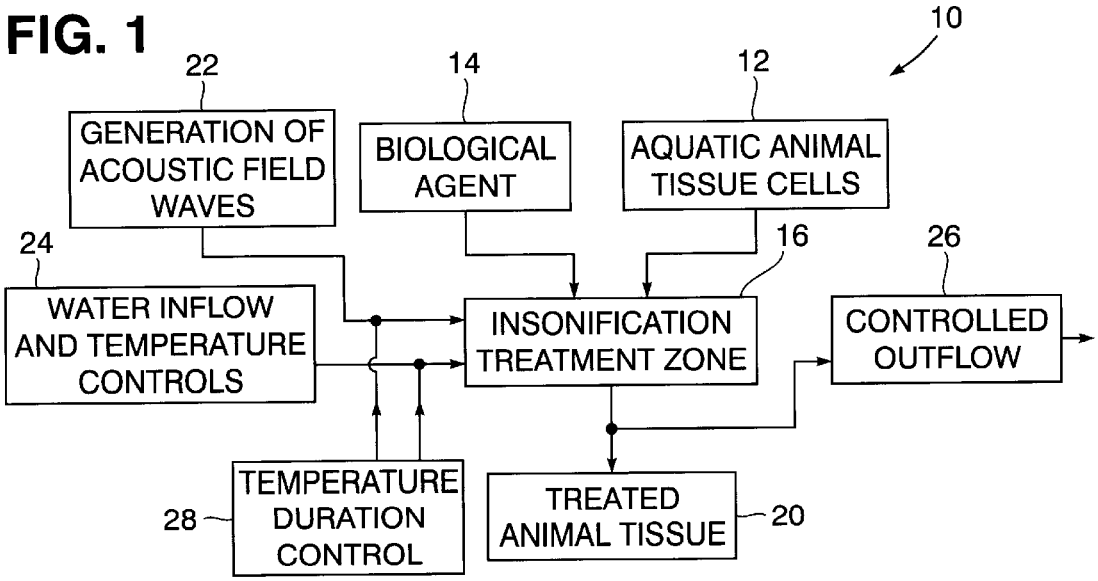
FIG. 1 is a block diagram schematically illustrating the process or method of the present invention.

Referring now to the drawing in detail, FIG. 1 diagrams the aquatic animal treatment method of the present invention, generally referred to by reference numeral 10. Pursuant to such method, the tissue cells 12 of aquatic animals to be treated such as migratory fish including rainbow trout as denoted in FIG. 1, are to be fused with a biological agent 14 by insonification which includes perforation and fusion performed within an underwater zone 16 during periods of limited duration so as to accommodate treatment of large populations of the aquatic animals. The agent 14 according to one embodiment is of a commonly used type from a group of tagging compounds including calcein (Fluorexine) and oxytetracyline hydrochloride (Terramycin) forming a solution with the water in the treatment zone 16 from which it is transferred to tissue cells such as the larvae and/or eggs of the fish being tagged. After completion of such treatment the tissue cells are removed from the treatment zone 16 and may undergo further processing such as washing so as to extract unfused agents from the treated tissues 20.

The foregoing referred to treatment within zone 16 is performed in response to establishment of an acoustic field therein by generation 22 of acoustic waves as denoted in FIG. 1 and under certain conditions established by water flow rate and temperature by controls 24 for inflow and temperature and controlled outflow 26 from the treatment zone 16. Timing of treatments within zone 16 are regulated by treatment duration control 28 applied to acoustic field energy generation 22 and controls 24 as also denoted in FIG. 1. As hereinafter indicated, treatment efficiency pursuant to the present invention is maximized by so limiting the treatment duration.

Figure 2:
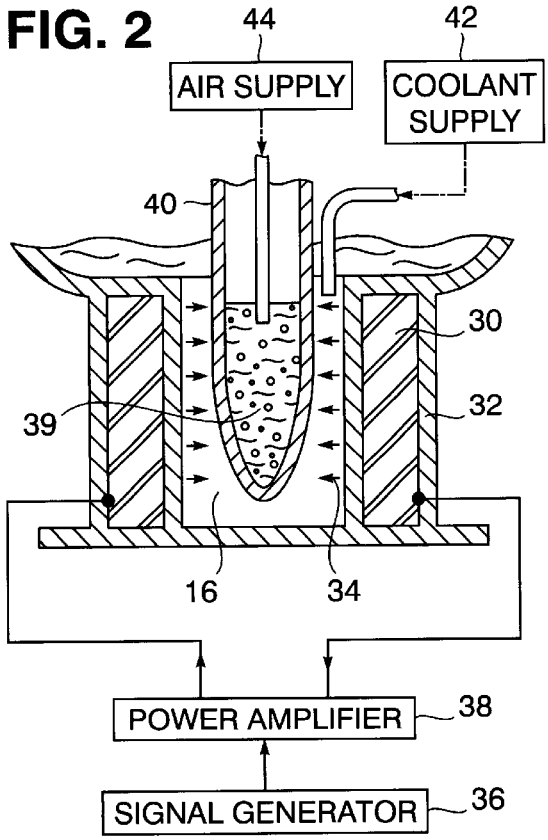
FIG. 2 is a partial section view and block diagram illustrating transducer conversion apparatus associated with the method depicted in FIG. 1.

The parameters of method 10 associated with the generation 22 of acoustic field waves for performance of the treatment, were obtained in connection with the use of apparatus as depicted in FIG. 2 showing treatment zone 16 enclosed by a cylindrical shaped transducer 30 within which water is confined. Such transducer 30 is of a piezoelectric type made of materials such as lead zirconium titanate ceramic (PZT), covered by a water protective coating 32. Such transducer 30 converts electrical energy supplied thereto into ultrasound energy in the form of acoustic waves 34 as symbolically denoted in FIG. 2, establishing the acoustic field within the water treatment zone 16. The electrical energy was converted by the transducer 30 into a steady state AC signal of approximately 40 kHz within a cavitation frequency range derived from a signal generator 36 and amplified to a voltage level of approximately 200 volts by a power amplifier 38 as denoted in FIG. 2. Such AC signal may be either continuous or pulsed having a selected duty cycle.

Fish eggs and/or larvae obtained from rainbow trout were exposed during experimental treatment to the foregoing described acoustic field within zone 16 by placement into a test tube 40, onto which the acoustic waves 34 are focussed as shown in FIG. 2, mixed with a body of seawater 39 having agent 14 dissolved therein. Such treatment was maximized by passage of a continuous flow of water from a coolant supply 42 to maintain the body of seawater 39 chilled to a predetermined constant temperature of 10° C., while air was injected into the seawater within the test tube by flow from air supply 44 forming bubbles therein during a limited treatment duration between 5 and 30 minutes. The test tube 40 was made of an acoustically transparent plastic material so as to accommodate exposure of its contents to the acoustic field generated during experimental treatment within zone 16 as hereinbefore described.

Figure 3:
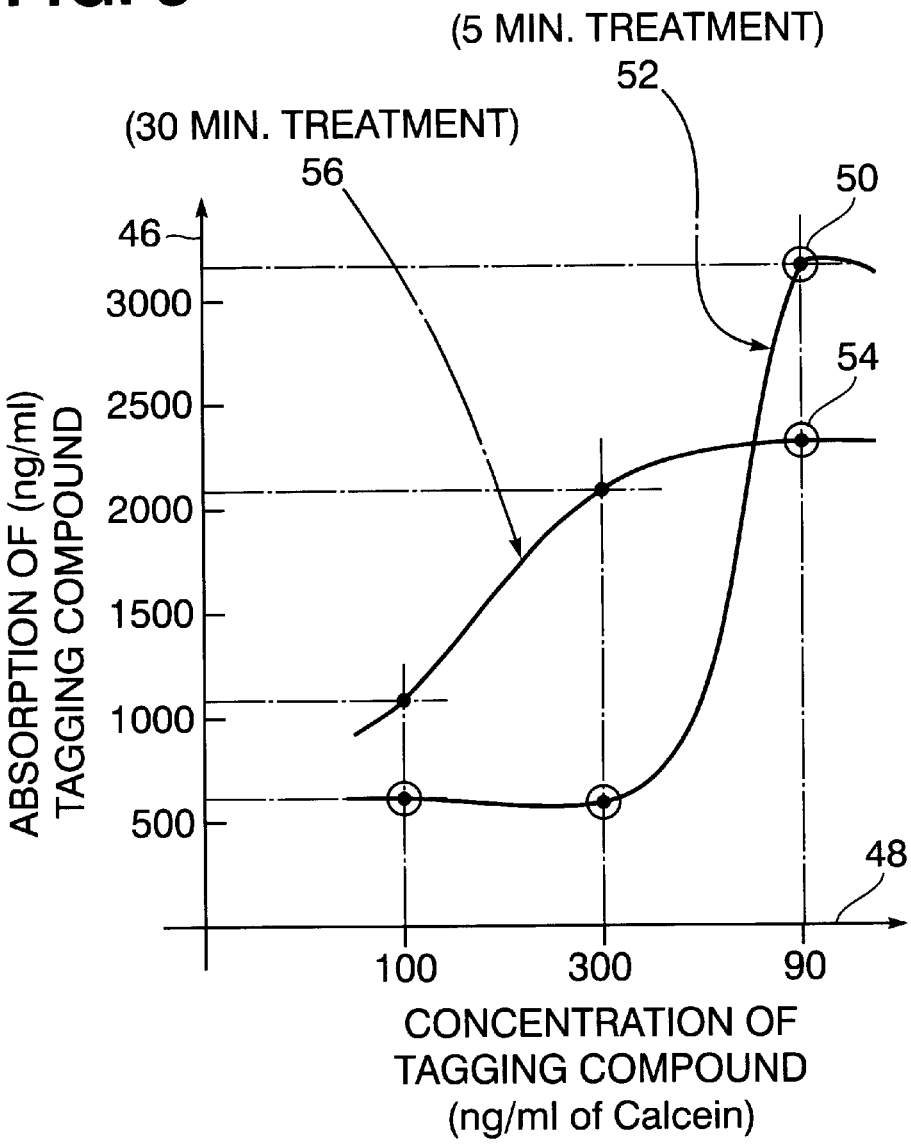
FIG. 3 is a graphical illustration of processing parameters from which maximized treatment duration is obtained.

From the foregoing referred to experimentation, various parameters of the method 10 were determined as graphically diagrammed in FIG. 3. Curved 52 in FIG. 3 depicts the variation in absorption by infusion of a tagging compound type of agent 14 into fish tissue cells as denoted on the vertical scale 46 for different concentrations of such tagging compound (calcein) as denoted on horizontal scale 48 during a 5 minute treatment duration. Such graphically depicted treatment reached maximized absorption at a peak point 50 on curve 52, for the same concentration of the tagging compound corresponding to a maximized absorption peak 54 on curve 56 for a 30 minute treatment duration. Accordingly, treatment is maximized by limiting its duration between 5 and 30 minutes under the conditions of flow, temperature and acoustic field energy within the treatment zone 16 as hereinbefore specified.

It should be understood that the transducer 30 may be replaced by a flat or curved plate type of transducer with which an unconfined body of water has the acoustic field disposed therein in contact with the transducer. Also, frequencies other than 40 kHz for the electrical energy converted to ultrasound energy by the transducer may be utilized, as long as it is within the cavitation frequency range. The fusion treatment was performed under the conditions described herein at a relatively high delivery rate causing detachment of the mucous membrane of the fish larvae. Such membrane is expected to grow back on the fish being tagged if maintained in a clean environment by washing for an adequate period of time following fusion treatment. Treatment for purposes other than tagging, such as DNA infusion, may be achieved by the present invention because of its capability for penetration of single living cells under the conditions described herein. The method of the present invention is therefore applicable to single cell organisms such as bacteria as well as plant cells.

Obviously, other modifications and variations of the present invention may be possible in light of the foregoing teachings. It is therefore to be understood that within the scope of the appended claims the invention may be practiced otherwise than as specifically described.

What is claimed is:

1. A method of treating aquatic animals by infusion of tissue cells thereof with a biological agent dissolved within a body of water in a treatment zone within which said infusion is performed, the improvement residing in the steps of: establishing an acoustic field of limited duration within said treatment zone during which said biological agent is transferred to the tissue cells; and regulating conditions of the body of water within the treatment zone to establish a constant temperature therein during said limited duration of the acoustic field under which said infusion occurs for absorption of the biological agent into the tissue cells.

2. The improvement as defined in claim 1 wherein said step of establishing an acoustic field comprises the steps of: generating steady state electrical signal energy having a frequency within a cavitation range; amplifying the steady state electrical signal energy to an operative voltage level and converting said amplified electrical signal energy into acoustical energy for producing said acoustic field within the treatment zone.

3. The improvement as defined in claim 2 wherein said biological agent is selected from a group of tagging compounds consisting of calcein and oxytetracyline hydrochloride.

4. The improvement as defined in claim 3 wherein said limited duration of the acoustic field is between 5 and 30 minutes during which said absorption of the biological agent in the tissue cells is maximized.

5. The method as defined in claim 4 wherein tissue cells consist of eggs and larvae of fish as the aquatic animals.

6. The improvement as defined in claim 1 wherein said step of regulating conditions of the body of water within the treatment zone includes: controlling flow rate of the water through said treatment zone; and cooling the body of water within the treatment zone for maintenance thereof at said constant temperature.

7. The improvement as defined in claim 1 wherein said biological agent is selected from a group including tagging and DNA transformation compounds.

8. A method applied to living cells for infusion with a biological agent within a water solution in an underwater treatment zone, comprising the steps of: generating steady state electrical signal energy within a cavitation frequency range amplified to a predetermined voltage level; converting said amplified electrical signal energy into acoustical energy for establishment of an acoustic field focussed on the living cells within said underwater treatment zone and regulating conditions within the treatment zone during said establishment of the acoustic field therein for transfer of the biological agent from the water solution to the living cells by controlling flow of water through said underwater treatment zone; and maintaining the water within said treatment zone at a constant temperature during said establishing of the acoustic field for a period of limited duration.

9. The method as defined in claim 8 wherein said constant temperature is 10° C. and said period of limited duration is between 5 and 30 minutes.

10. The method as defined in claim 9 wherein said biological agent is selected from a group of tagging compounds consisting of calcein and oxytetracyline hydrochloride.

11. The method as defined in claim 10 wherein said electrical signal energy has a frequency of approximately 40 kHz and said predetermined voltage level of the amplified signal energy is approximately 200 volts.

12. A method for treatment of living tissue cells by infusion of a tagging compound selected from the group consisting of calcein and oxytetracyline hydrochloride into the tissue cells from a body of water within which the tagging compound is dissolved, the improvement residing in the steps of: establishing an acoustic field within said treatment zone during a period of limited duration of 5 to 30 minutes; and inducing flow of said body of water through the treatment zone during said period of limited duration at a flow rate regulated to maintain a constant temperature of 10° C. within the treatment zone under which said infusion occurs to maximize absorption of the tagging compound within the living tissue cells.

* * * * *